(12) United States Patent
Cash

(10) Patent No.: US 11,426,374 B2
(45) Date of Patent: Aug. 30, 2022

(54) MODIFICATION OF THE PH AND OTHER PHYSICAL PROPERTIES OF OXALOACETIC ACID TO ALLOW FOR ENHANCED STABILITY AND MULTIPLE DELIVERY SYSTEMS

(71) Applicant: Terra Biological LLC, San Diego, CA (US)

(72) Inventor: Alan B. Cash, San Diego, CA (US)

( * ) Notice: Subject to any disclaimer, the term of this patent is extended or adjusted under 35 U.S.C. 154(b) by 94 days.

(21) Appl. No.: 15/042,393

(22) Filed: Feb. 12, 2016

(65) Prior Publication Data

US 2016/0235696 A1 Aug. 18, 2016

Related U.S. Application Data

(60) Provisional application No. 62/115,369, filed on Feb. 12, 2015.

(51) Int. Cl.
| | | |
|---|---|---|
| *A61K 31/194* | (2006.01) | |
| *A61K 47/02* | (2006.01) | |
| *A61K 9/00* | (2006.01) | |
| *A61K 47/26* | (2006.01) | |
| *A61K 9/20* | (2006.01) | |
| *A61K 47/12* | (2006.01) | |
| *A61K 47/14* | (2017.01) | |
| *A23L 33/10* | (2016.01) | |
| *A23L 27/00* | (2016.01) | |
| *B65D 79/00* | (2006.01) | |
| *G01N 33/15* | (2006.01) | |
| *B65D 1/02* | (2006.01) | |

(52) U.S. Cl.
CPC ............ *A61K 31/194* (2013.01); *A23L 27/86* (2016.08); *A23L 33/10* (2016.08); *A61K 9/006* (2013.01); *A61K 9/0056* (2013.01); *A61K 9/20* (2013.01); *A61K 47/02* (2013.01); *A61K 47/12* (2013.01); *A61K 47/14* (2013.01); *A61K 47/26* (2013.01); *B65D 79/0081* (2020.05); *G01N 33/15* (2013.01); *B65D 1/0261* (2013.01); *B65D 2201/00* (2013.01)

(58) Field of Classification Search
CPC ............................. B65D 79/008; B65D 79/005
See application file for complete search history.

(56) References Cited

U.S. PATENT DOCUMENTS

| | | | | |
|---|---|---|---|---|
| 3,833,142 A | * | 9/1974 | Owen et al. | ................... 215/351 |
| 5,727,710 A | * | 3/1998 | Severus | ............... B65D 79/005 |
| | | | | 220/609 |
| 2010/0234436 A1 | * | 9/2010 | Dairiki | ................... A01N 25/04 |
| | | | | 514/373 |
| 2011/0064679 A1 | | 3/2011 | Cash | |
| 2013/0143930 A1 | | 6/2013 | Cash | |

OTHER PUBLICATIONS

Herb Nutritionals, Oxaloacetic acid, 2019, http://herbnutritionals.com/nutraceuticals/oxaloacetic-acid (Year: 2019).*
DDW the Color House, Calcium Carbonate, 2019, http://www.ddwcolor.com/natural-colours/calcium-carbonate/ (Year: 2019).*
PubChem, Pentaerythritol, 2005, https://pubchem.ncbi.nlm.nih.gov/compound/8285 (Year: 2005).*
IndiaMART, Di Calcium Phosphate, 2019, https://www.indiamart.com/proddetail/di-calcium-phosphate-6737966512html (Year: 2019).*
ICF International for the USDA National Organic Program, Ascorbyl Palmitate Handling/Processing Technical Evaluation Report, 2012, pp. 1-12 (Year: 2012).*
European Search Report dated Jun. 30, 2016 issued by the European Patent Office in corresponding EP Application No. 16155572.7.

* cited by examiner

*Primary Examiner* — Savitha M Rao
*Assistant Examiner* — Gregg Polansky
(74) *Attorney, Agent, or Firm* — Sughrue Mion, PLLC

(57) ABSTRACT

The present invention relates to oxaloacetic acid preparations and the use of hygroscopic components to prevent decomposition of the oxaloacetic acid. These compounds can then be made into sublingual lozenges and buccal lozenges to serve as nutritional supplements, medical foods or drugs. These compounds can also be used in the manufacture of oxaloacetic acid preparations in transdermal patches, inhalation preparations and anal or vaginal suppositories. Also provided are simple inexpensive tests to monitor the decomposition of oxaloacetic acid in compositions.

13 Claims, No Drawings

MODIFICATION OF THE PH AND OTHER PHYSICAL PROPERTIES OF OXALOACETIC ACID TO ALLOW FOR ENHANCED STABILITY AND MULTIPLE DELIVERY SYSTEMS

FIELD OF THE INVENTION

The present invention relates to oxaloacetic acid preparations and the use of hygroscopic components to prevent decomposition of the oxaloacetic acid. These compounds can then be made into sublingual lozenges and buccal lozenges to serve as nutritional supplements, medical foods or drugs. These compounds can also be used in the manufacture of oxaloacetic acid preparations in transdermal patches, inhalation preparations and anal or vaginal suppositories. Also provided are simple inexpensive tests to monitor the decomposition of oxaloacetic acid in compositions.

BACKGROUND

Oxaloacetic Acid has been shown to be a commercial nutritional supplement and medical food, selling around the world as "benaGene", "CRONaxal" and other labels licensed from Terra Biological LLC. It is currently in clinical trial for a drug for mitochondrial disease, Parkinson's disease, Alzheimer's disease and Cancer. Initially this compound was not used as a nutritional supplement, medical food or drug due to very serious stability problems. Oxaloacetate commercially produced needs to be stored at $-10$ to $-20$ degrees, unless manufactured in the enol-oxaloacetate form, with water content less than 2%, and isolation from water sources (such as the atmosphere or other ingredients). (See Cash, U.S. patent application Ser. No. 13/806,465). Water catalyzes the conversion of enol-oxaloacetate to the lower energy state of the keto-oxaloacetate, which then spontaneously decays into pyruvate and carbon dioxide, which makes it difficult to use as a nutritional supplement, medical food or drug.

Certain compounds are also not stable with oxaloacetic acid. Yoshikawa [Kiyohiko Yoshikawa, "Studies on Antidiabetic Effect of Sodium Oxaloacetate", Tohoku J. Exp. Med., 1968, 96, p127-141] teaches that oxaloacetic acid is not stable at all, and is made stable by creating the sodium salt of oxaloacetate. Cash, 2013, later teaches that sodium oxaloacetate is not stable, and quickly degrades at room temperature.

Krebs [H. A. Krebs, "The Effect of Inorganic Salts on the Ketone Decomposition of Oxaloacetic Acid", Biochem. 1942, 36, p 303-05] shows that the cations cause the decomposition, specifically multi-valent cations including Calcium, Magnesium, Barium, Zing, Silver, Mercury, Copper, Manganese, Cadmium, Iron, Lead and Aluminum.

Notably, Krebs found that sodium and potassium were not effective in accelerating the decomposition of oxaloacetate.

Speck [J F Speck, "The effect of cations on the decarboxylation of oxaloacetic acid", J Biol Chem, 1949 March, 178(1):p315-24] teaches that divalent cations also catalyze the conversion from enol-oxaloacetate to keto-oxaloacetate, allowing the keto form to quickly degrade into pyruvate and carbon dioxide. Divalent cations have a valence of 2, and include Cadmium, Calcium, Chromium (II), Cobalt (II), Copper (II), Iron (II), Lead, Magnesium, Manganese (II), Mercury (II), Nickel (II), Strontium, Tin (II), and Zinc. Speck also found that Aluminum, Lanthanum (III), and Iron (III), trivalent compounds, were also found to speed the decarboxylation of oxaloacetate. Speck specifically notes that the decarboxylation is most effective with "a considerable number of divalent positive ions, including Cu++, Pb++, Ba++, Mg++, Fe++, Ni++, Ca++, Cd++, Co++, and Mn++ . . . ."

Kornberg [Kornberg A, Ochoa S, Mehler A, "Spectrophotometic Studies on the Decarboxylation of beta-Keto Acids", Journal of Biol Chem, 1948, 174:159-172] also found that Aluminum, Magnesium and Manganese cause oxaloacetic acid to quickly decarboxylate into pyruvate and carbon dioxide.

Although Cash has solved the problem of oxaloacetate stability in an oral preparation, such preparations have their drawbacks. Yoshikawa tested an oral preparation of sodium oxaloacetate on three patients, and found that the 200 mg of oxaloacetate was found in the bloodstream after 1 hour, in amounts that calculate out to be about 2 to 5% of the dose provided.

In some cases, such as athletic competitions or for various diseases or conditions such as cancer, Parkinson's, closed head injury, stroke or Alzheimer's Disease treatments, it is desirable to both have the oxaloacetate available faster in the bloodstream, and at higher dosages than are generated by oral supplementation. In this case, intravenous (IV) supplementation can be implemented with freshly prepared pH balanced solutions of oxaloacetate that are given quickly to the patient prior to the decarboxylation of the oxaloacetate. Cash describes a biphasic IV devise for this purpose. IV supplementation, however, is not convenient unless in a medical setting, which limits its usability.

Other methods of delivery are transdermal patches, sublingual lozenges, buccal lozenges, inhalation preparations and anal or vaginal suppositories. These methods of delivery can provide higher percentages of the given oxaloacetate to the blood stream for distribution to various organs, and provide the oxaloacetate quicker than the oral route. These delivery methods face a problem with the acidity of oxaloacetic acid. As an example of this, oxaloacetic acid delivered to the mouth in powder or lozenge form creates a solution at a pH of approximately 2.3. This low pH degrades the enamel on the teeth, and provides a large challenge to continued long-term use of oxaloacetate in sublingual lozenges and buccal lozenges. The effect on the teeth is apparent after just 100 mg oxaloacetate is taken either sublingually or via buccal lozenge. The low pH also causes a painful burning sensation in the lungs if inhaled. Vaginal and anal suppositories are also uncomfortable at low pH. Transdermal patches at low pH are also uncomfortable.

So it would be desirable to find a pH modifier and other physical modifiers of oxaloacetic acid to allow development of different delivery systems with stable oxaloacetate preparations.

SUMMARY OF THE INVENTION

Viewed from a first aspect, the invention provides a method of adjusting the pH of an oxaloacetic acid composition without inducing decarboxylation of said oxaloacetic acid by the addition of a hygroscopic basic compound, optionally wherein said hygroscopic basic compound is a calcium carbonate and/or is a white color.

Viewed from a second aspect, the invention provides a combination of matter consisting of an oxaloacetic acid combined with a hygroscopic basic compound for the adjustment of pH, optionally wherein said hygroscopic basic compound is a calcium carbonate. Alternatively, according to variants of the second aspect, the invention provides a combination of matter comprising an oxaloacetic acid combined with a hygroscopic basic compound for the adjustment of pH, optionally wherein said hygroscopic basic compound is a calcium carbonate. According to further variants of the second aspect, the invention provides a combination of matter consisting essentially of an oxaloacetic acid combined with a hygroscopic basic compound for the adjustment of pH, optionally wherein said hygroscopic basic compound is a calcium carbonate.

Viewed from a third aspect, the invention provides a method to adjust the taste of an oxaloacetic acid composition to reduce bitterness by the addition of a hygroscopic sweetener, optionally wherein said hygroscopic sweetener is a Erythitol.

Viewed from a fourth aspect, the invention provides a combination of matter consisting of an oxaloacetic acid combined with a hygroscopic sweetener compound to reduce bitterness, optionally wherein said hygroscopic sweetener is a Erythitol. Alternatively, according to variants of the fourth aspect, the invention provides a combination of matter comprising an oxaloacetic acid combined with a hygroscopic sweetener compound to reduce bitterness, optionally wherein said hygroscopic sweetener is a Erythitol. According to further variants of the fourth aspect, the invention provides a combination of matter consisting essentially of an oxaloacetic acid combined with a hygroscopic sweetener compound to reduce bitterness, optionally wherein said hygroscopic sweetener is a Erythitol.

Viewed from a fifth aspect, the invention provides a method of producing a compactable lozenge or tablet of an oxaloacetic acid composition without inducing decarboxylation of said oxaloacetic acid by the addition of a hygroscopic binder agent, optionally wherein said hygroscopic binder agent is a Dicalcium Phosphate dibasic.

Viewed from a sixth aspect, the invention provides a combination of matter consisting of an oxaloacetic acid combined with a hygroscopic binder agent to create a lozenge or tablet, optionally wherein said hygroscopic binding agent is a Dicalcium Phosphate dibasic. Alternatively, according to variants of the sixth aspect, the invention provides a combination of matter comprising an oxaloacetic acid combined with a hygroscopic binder agent to create a lozenge or tablet, optionally wherein said hygroscopic binding agent is a Dicalcium Phosphate dibasic. According to further variants of the sixth aspect, the invention provides a combination of matter consisting essentially of an oxaloacetic acid combined with a hygroscopic binder agent to create a lozenge or tablet, optionally wherein said hygroscopic binding agent is a Dicalcium Phosphate dibasic.

Viewed from a seventh aspect, the invention provides a method of producing a compactable lozenge or tablet of an oxaloacetic acid composition without inducing decarboxylation of said oxaloacetic acid by the addition of a hygroscopic release agent, optionally wherein said hygroscopic release agent is a Vegetable Stearic Acid, or an Ascorbyl Palmitate, or a combination of both.

Viewed from an eighth aspect, the invention provides a combination of matter consisting of an oxaloacetic acid combined with a hygroscopic release agent to create a lozenge or tablet, optionally wherein said hygroscopic release agent is either a Vegetable Stearic Acid, or an Ascorbyl Palmitate, or a combination of both. Alternatively, according to variants of the eighth aspect, the invention provides a combination of matter comprising an oxaloacetic acid combined with a hygroscopic release agent to create a lozenge or tablet, optionally wherein said hygroscopic release agent is either a Vegetable Stearic Acid, or an Ascorbyl Palmitate, or a combination of both. According to further variants of the eighth aspect, the invention provides a combination of matter consisting essentially of an oxaloacetic acid combined with a hygroscopic release agent to create a lozenge or tablet, optionally wherein said hygroscopic release agent is either a Vegetable Stearic Acid, or an Ascorbyl Palmitate, or a combination of both.

Viewed from a ninth aspect, the invention provides a method to detect the decomposition of an oxaloacetic acid composition in a sealed container, without the need to open the sealed container, by detecting a bulge in the packaging, optionally wherein said sealed container can spin freely due to said bulge to detect said oxaloacetic acid decomposition or wherein said bulge in said sealed container is a popup button.

Viewed from a tenth aspect, the invention provides a method to detect the decomposition of an oxaloacetic acid composition by comparing the color of said composition to a calibrated color chart, optionally where said color chart is printed on a container holding said oxaloacetic acid composition.

Viewed from an eleventh aspect, the invention provides a combination of matter comprised of an oxaloacetic acid with a set of other components, wherein said set of other components consist of white compounds, allowing said combination of matter to be measured for said oxaloacetic acid decomposition with a calibrated color chart.

Viewed from a twelfth aspect, the invention provides a combination of matter comprised of an oxaloacetic acid in combination with one or more components selected from a group of a hygroscopic pH modifier, a hygroscopic taste modifier, a hygroscopic binding agent, and a hygroscopic release agent, optionally in which the components selected from said group are a calcium carbonate, a di-calcium phosphate, a vegetable steric acid, an Ascorbyl Palmitate, and a erythitol; and/or the components selected from said group are all white powders to allow the user to see any color changes in said combination of matter to ascertain oxaloacetic acid decomposition; and/or within the combination is protected from water moisture with a sealed container for the purpose of a nutritional supplement, a medical food, or a drug.

DETAILED DESCRIPTION

It would seem to be a simple and obvious matter to adjust the pH of oxaloacetic acid so that it can be used in a variety of delivery systems including transdermal patches, sublingual lozenges, buccal lozenges, inhalation preparations and anal or vaginal suppositories. Krebs specifically notes that "Univalent cations (Na, K, Ag) are inactive" in accelerating the decomposition of oxaloacetic acid. Thus, one skilled in the art could conceive of common solutions of NaOH or KOH to adjust the pH. However, solutions of these compounds contain water, which also acts as a catalyst to allow enol-oxaloacetate to change to keto-oxaloacetate, and subsequent decarboxylation into Pyruvate and Carbon Dioxide takes place spontaneously, destroying the oxaloacetate within a few days. The skilled artisan would then conceive of mixtures of oxaloacetic acid powder and anhydrous NaOH or KOH as a method to raise pH and yet preserve the oxaloacetic acid.

The Applicant followed just this line of reasoning, and prepared sublingual lozenges that contained oxaloacetate with either anhydrous NaOH or KOH or both as a pH modifying agent. To the surprise of the Applicant, the sublingual tablets of oxaloacetic acid and either NaOH or KOH or both degraded within a few days of manufacture.

This is an unanticipated problem, not revealed by the prior art, which suggests that such lozenges should be stable with anhydrous preparations of univalent compounds.

The Applicant also noticed that as the pH of oxaloacetate was brought towards a neutral pH of 7, the taste of the oxaloacetate preparation became extremely bitter, another unanticipated problem, not revealed by the prior art. Taste modification would be needed for sublingual and buccal lozenges.

A further problem noticed is that some binding agents caused the oxaloacetic acid to degrade. Binding agents are required because compressed oxaloacetate powders are very friable, another unrecognized problem not known in the prior art. Release agents and flavoring agents further caused rapid deterioration of oxaloacetic acid.

Oxaloacetic acid is highly unstable, which is most probably why it has not been used as a nutritional supplement, medical food or drug until just recently, based on the discoveries of the Applicant Cash.

The Applicant set out on a path of discovery to ascertain what compounds would be stable with oxaloacetic acid—not just for pH modification, but for other physical properties necessary for various delivery systems, such as color stabilization, lozenge dissolve time, lozenge friability, taste, lozenge release from the tablet mold, flow agents, and bulking agents in addition to pH modification. Preparations of oxaloacetic acid was compounded with various ingredients and compressed into a lozenge for examination over a period of one week. Here are compounds that caused rapid decomposition of oxaloacetate:

- KOH (pH modifier)
- NaOH (pH modifier)
- Calcium Phosphate Dibasic (pH modifier and buffer)
- Potassium Bicarbonate (pH modifier)
- Sodium bicarbonate (pH modifier)
- Magnesium Hydroxide (pH modifier)
- Magnesium Oxide (pH modifier)
- TiO2 (color modifier)
- Gelatin capsules (delivery modifier—water content too high) Note: not compressed, powder inside capsule
- Rice Flour (bulking agent—water content too high)
- Corn Starch (bulking agent—water content too high)
- Silicon Dioxide (bulking agent)
- Potassium Citrate (taste modifier)
- Citric Acid (taste modifier)
- Stevia (taste modifier)
- Xylitol (taste modifier)
- NaCl (taste modifier)
- Table sugar (taste modifier)
- Magnesium Stearate (lozenge release agent)

As most of these compounds are common in the manufacture of transdermal patches, sublingual lozenges, buccal lozenges, inhalation preparations and anal or vaginal suppositories, this caused a major problem in the development of these delivery systems.

It was determined by the Applicant that the problem with many of these potential modifiers to oxaloacetic acid compositions was that many of these compounds were hygroscopic—they attracted and collected water. This attraction of water quickly lead to the catalyzation of enol-oxaloacetate to keto-oxaloacetate and the subsequent decarboxylation of the oxaloacetate into pyruvate and carbon dioxide. This was especially a problem in sublingual and buccal lozenge preparations, because it is common practice to place multiple lozenges in a single package. When the package is opened, the non-used lozenges are exposed to the atmosphere and water vapor which can cause them to decompose.

The Applicant found the following compounds to be effective additives to oxaloacetic acid preparations to minimize degradation:

- Calcium Carbonate (pH Modifier)
- Erythitol (Taste Modifier)
- Dicalcium Phosphate dihydrate (pH Modifier and lozenge binder)
- Vegetable Steric Acid (Release Agent)
- Ascorbyl Palmitate (Release Agent)

It is interesting that these compounds work successfully with oxaloacetic acid. Krebs, Kornberg and Speck all teach against using divalent cations such as Calcium with oxaloacetic acid. In contrast to the teaching of prior art, the Applicant found Calcium Carbonate to be an effective way of increasing the pH without degrading the oxaloacetic acid. Interestingly, both potassium bicarbonate and sodium bicarbonate were not effective and potassium hydroxide and sodium hydroxide were not effective. NaOH, KOH, KHCO3, NaHCO3 are all hygroscopic compounds which pull water in from the atmosphere, and create a catalytic decomposition of the oxaloacetate.

DiCalcium Phosphate dehydrate contains water, so it was against the teaching of prior art that this compound could be used successfully with oxaloacetic acid. Apparently, it could be used because the water is so tightly held by the DiCalcium Phosphate molecule, that the water does not interact with the oxaloacetic acid.

Erythitol is a sugar alcohol that is nonhygroscopic. Xylitol, is known to be hygroscopic, which explains why it did not work well with oxaloacetic acid.

Vegetable Steric Acid and Ascorbyl Palmitate are non-hygroscopic compounds.

Thus, the Applicant has found an answer to problems which were unknown in the prior art, namely, how to modify the pH and physical properties of oxaloacetic acid preparations, without the degradation of the oxaloacetic acid. Applicant submits that modifiers to oxaloacetic acid by addition of non-hygroscopic elements allow the preparation of useful delivery agents for oxaloacetic acid for use in nutritional supplements, medical foods and drugs.

Applicant first modifies pH with the non-hygroscopic calcium carbonate. This causes the taste of oxaloacetate preparation to become bitter. Applicant next modifies the bitter taste of pH modified oxaloacetate by adding a non-hygroscopic sweetener, Erythitol, solving a problem was that unknown in the prior art. Applicant next provides suitable compounds to bind the composition with non-hygroscopic Dicalcium Phosphate dihydrate. Lastly, the Applicant provides non-hygroscopic release agents so that the compressed lozenge can be removed easily from the manufacturing equipment. Vegetable Steric Acid and Ascorbyl Palmitate are used as release compounds.

While the specific components of a sublingual or buccal lozenge have been described in this specification, these same components can be used in transdermal patches, inhalation preparations and anal or vaginal suppositories to provide better product stability with oxaloacetic acid.

Building a product that is stable is important. It is also important to demonstrate to the customer that the product has not degraded. We do this routinely by inscribing a "batch number" on each bottle, and an expiration date. The expiration date is based on chemical stability analysis over time. Currently, we show a 2-year shelf life with our oxaloacetate products.

In order to build further customer and distributor confidence, there are simple tests that they can perform to assure oxaloacetic acid stability. While this is now new in the art (batteries have a testing strip impregnated into their store packaging), this is a new concept for nutritional supplements, and specifically a new test for oxaloacetate compounds. One test for product quality that can be performed without opening the bottle of supplements is the "Spin Test". Because one of the degradation of oxaloacetic acid is carbon dioxide, any closed container will experience an increase in partial pressure due to the creation of the gas. This increase in partial pressure is enough to "bulge" the bottom of PVC bottles, which are often used in the packaging of oxaloacetic acid products. The bulge occurs at the bottom of the bottle because the round sides and rounded top each act as an "arc" with greater structural strength. The weak point, from a structural standpoint is the bottom of the bottle. When the bottom bulges outward due to increased interior pressure, the bottle can be easily "spun" on the bottom bulge. Bottles without this bulge do not spin easily, if at all. This not only allows the consumers a quick and easy test, it is also effective for providers of this product to check their stock for freshness without needing to open the container or perform expensive chemical tests. Alternately, a package can contain a "weak spot" that bubbles when freshness of the product is gone, also known as a "popup" button.

When the bottle is open, it is subjected to moisture from the atmosphere. Although the components of this formulation have been chosen to be non-hygroscopic, excess humidity can still degrade the open product. As oxaloacetate degrades to carbon dioxide and pyruvate, it changes color. Initially brilliant white, it takes on a yellowish tinge at first, then turns completely yellow, then a dark orange, then brown. By putting a calibrated color comparison chart on the back of the bottle, the consumer can assure themselves that the product is still in the "good-range" (white to slightly yellow) by comparing the lozenge or product with the color chart. This works if the other ingredients added to oxaloacetic acid are also white. Calcium Carbonate, Erythitol, Dicalcium Phosphate dehydrate, Vegetable Steric Acid, and Ascorbyl Palmitate are all white. The calibration of the color chart is obtained by exposing the oxaloacetic acid composition to a very humid environment for different periods of time, and taking color photographs of the composition. Degradation of the oxaloacetic acid composition is stopped at various color points by freezing the composition. The various colored compositions are then evaluated by gas chromatography to ascertain the amount of remaining oxaloacetic acid in the composition, and each color is assigned a value.

EXAMPLES

While in the following, the present invention is described in further detail with reference to Examples, the present invention is not limited to any of them by no means.

Example 1

A lozenge is created consisting of 100 mg oxaloacetic acid, and 100 mg of a test substance. The powders are compressed in a tablet mold and released. Each test tablet is placed on a cardboard for one week to ascertain stability in an open environment, such as an open bottle. The substances tested included the following:
  KOH (pH modifier)
  NaOH (pH modifier)
  Calcium Phosphate Dibasic (pH modifier and buffer)
  Potassium Bicarbonate (pH modifier)
  Sodium bicarbonate (pH modifier)
  Magnesium Hydroxide (pH modifier)
  Magnesium Oxide (pH modifier)
  TiO2 (color modifier)
  Gelatin capsules (delivery modifier—water content too high) NOTE: No compression, just filled capsule
  Rice Flour (bulking agent—water content too high)
  Corn Starch (bulking agent—water content too high)
  Silicon Dioxide (bulking agent)
  Potassium Citrate (taste modifier)
  Citric Acid (taste modifier)
  Stevia (taste modifier)
  Xylitol (taste modifier)
  NaCl (taste modifier)
  Table sugar (taste modifier)
  Magnesium Stearate (lozenge release agent)

In each case, the oxaloacetic acid turned from white, to yellow, to orange to brown as the oxaloacetic acid decomposed to pyruvate and carbon dioxide. In several cases, bubbles of carbon dioxide could be seen on the decomposing tablet.

Example 2

The procedure in Example 1 was followed, but with the following individual modifiers to oxaloacetic acid:
  Calcium Carbonate (pH Modifier)
  Erythitol (Taste Modifier)
  Dicalcium Phosphate dihydrate (pH Modifier and lozenge binder)
  Vegetable Steric Acid (Release Agent)
  Ascorbyl Palmitate (Release Agent)

When oxaloacetic acid is combined with the above powdered agents and compressed, the lozenge remains white without bubbles for at least one week's time, even in humid conditions.

Example 3

1,000 mg of oxaloacetic acid were combined with 1,000 mg calcium carbonate, and thoroughly mixed in a flask. Off gas from the flask was captured and measured. In two months, no carbon dioxide (or any other gas) was captured from the mixture, indicating long term compatibility in a sealed environment.

Example 4

A lozenge tablet was created using 100 mg anhydrous oxaloacetic acid, 80 mg ascorbic acid, 15 mg Ascorbyl Palmitate, 100 mg calcium carbonate, 74.2 mg Di-Calcium Phosphate, 35 mg vegetable stearic acid, 75 mg Erythitol. The tablet was compressed, then stored in a moisture-proof vial. Stability tests indicated that the product was highly stable, with little or no oxaloacetic acid decomposition after 3 months.

Example 5

A sublingual lozenge tablet was created as per Example 4. The tablet was stored in a sealed, 50 cc high density plastic bottle with a flat bottom. If carbon dioxide were to be generated from the breakdown of oxaloacetic acid, the bottom of the bottle would have bulged, and the bottle would easily spin on the bulged bottom. The bottle did not spin after 3 months. Upon opening the bottle, the color of the lozenge tablet was compared to a calibrated color chart printed on the back of the bottle. The color of the lozenge tablet was white, indicating no decomposition of oxaloacetic acid.

While the illustrative embodiments of the present invention are provided in the above description, such is for illustrative purpose only and it is not to be construed restrictively. Modification and variation of the present invention that will be obvious to those skilled in the art is to be covered by the following claims.

The invention claimed is:

1. An oxaloacetic acid preparation with reduced decarboxylation of said oxaloacetic acid as a dietary supplement, a medical food or a drug, comprising a mixture of an oxaloacetic acid, a non-hygroscopic pH modifier, a non-hygroscopic taste modifier, a non-hygroscopic binder agent, and a non-hygroscopic release agent, wherein the non-hygroscopic pH modifier is a calcium carbonate, the non-hygroscopic binder agent is a dicalcium phosphate dihydrate, the non-hygroscopic taste modifier is an erythritol, and the non-hygroscopic release agent includes vegetable stearic acid and ascorbyl palmitate.

2. The oxaloacetic acid preparation according to claim 1, wherein the preparation is contained in a sealed PVC bottle with a flat flexible bottom that moves outward with increasing pressure within the bottle.

3. The oxaloacetic acid preparation according to claim 1, further comprising a sealed container surrounding the mixture.

4. The oxaloacetic acid preparation according to claim 1, wherein the mixture is in a form of a lozenge or tablet.

5. A method of producing the oxaloacetic acid preparation according to claim 1, comprising the step of mixing the oxaloacetic acid with the non-hygroscopic pH modifier, the non-hygroscopic taste modifier, the non-hygroscopic release agent, and the non-hygroscopic binder agent, wherein decarboxylation of said oxaloacetic acid does not occur during the method.

6. The method of claim 5, further comprising the step of forming the mixture into a tablet or lozenge.

7. The method of claim 5, further comprising sealing the mixture in a container.

8. A method to detect decomposition of the mixture in the oxaloacetic acid preparation of claim 2, comprising a step of detecting a bulge in the sealed bottle, wherein said method does not include a step of opening the sealed bottle.

9. The method according to claim 8, further comprising determining whether said bulge permits the sealed bottle to spin freely.

10. The method according to claim 9 wherein said bulge in said sealed bottle is a popup button.

11. A method to detect decomposition of the mixture in the oxaloacetic acid preparation of claim 1, comprising a step of comparing the color of said oxaloacetic acid composition to a calibrated color chart.

12. A method to detect decomposition of the mixture in the oxaloacetic acid preparation of claim 2, wherein a calibrated color chart is printed on the sealed bottle, said method comprising a step of comparing the color of said oxaloacetic acid composition to the calibrated color chart.

13. The oxaloacetic acid preparation according to claim 1, further comprising a sealed bottle with a weak spot that bubbles with increasing pressure.

* * * * *